Figure 1A:
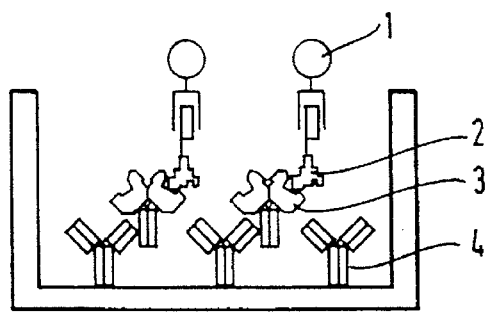

United States Patent [19]

Lauffer et al.

[11] Patent Number: 5,639,597
[45] Date of Patent: Jun. 17, 1997

[54] CELL-FREE RECEPTOR BINDING ASSAYS, THE PRODUCTION AND USE THEREOF

[75] Inventors: Leander Lauffer, Marburg; Gerd Zettlmeissl, Wetter; Patricia Oquendo, Marburg, all of Germany

[73] Assignee: Behringwerke Aktiengesellschaft, Marburg, Germany

[21] Appl. No.: 243,010

[22] Filed: May 13, 1994

Related U.S. Application Data

[63] Continuation of Ser. No. 110,798, Aug. 23, 1993, abandoned, which is a continuation of Ser. No. 798,564, Nov. 26, 1991, abandoned.

[30] Foreign Application Priority Data

Nov. 28, 1990 [DE] Germany ............... 40 37 837.3

[51] Int. Cl.$^6$ ............... C12Q 1/70; C12Q 1/28; C12Q 1/42; C12Q 1/66; G01N 33/543
[52] U.S. Cl. ............... 435/5; 435/7.2; 435/7.5; 435/7.8; 435/7.92; 435/28; 436/518
[58] Field of Search ............... 435/5, 7.1, 7.2, 435/7.21, 7.8, 7.94, 969, 972, 7.5, 7.92, 28; 436/518, 547, 817; 530/387.3, 817

[56] References Cited

U.S. PATENT DOCUMENTS

| | | | |
|---|---|---|---|
| 4,859,609 | 8/1989 | Dull et al. | 436/501 |
| 5,116,964 | 5/1992 | Capon et al. | 536/23.5 |

FOREIGN PATENT DOCUMENTS

| | | |
|---|---|---|
| 0314317 | 5/1989 | European Pat. Off. |
| 0325262 | 7/1989 | European Pat. Off. |
| 0330977 | 9/1989 | European Pat. Off. |
| 4020607.6 | 6/1990 | Germany |

OTHER PUBLICATIONS

Sankolli et al., Improvement in the antibody binding characteristics of microtitre wells by pretreatment with anti–IgG Fc immunoglobulin. Journal of Immunological Methods 104:191–194, 1987.

Watson et al., J. Cell Biol 110:2221–2229, 1990.

Ashkenagi et al., Proc. Natl. Acad. Sci. 87:7150–7154, 1990.

Radioiodination of Interleukin 2 to High Specific Activities by the Vapor–Phase Chloramine T Method, by John J. Siekierka and Steven DeGudicibus, Analyt. Biochem. 172:514–517, Feb. 25, 1988.

Nonradioactive Ligand Binding Assay for Epidermal Growth Factor by Ivan C. King and Joseph J. Catino, Analyt. Biochem. 188:97–100, Nov. 5, 1990.

"Visualization of Binding Sites for Bovine Parathyroid Hormone (PTH 1–84) on Cultured Kidney Cells With a Biotinyl–b–PTH(1–84) Antagonist 1,2", by A. Niendork, et al., J. Histochem. Cytochem. 34(3): 357–361, 1986.

"A Receptor for Tumor Necrosis Factor Defines an Unusual Family of Cellular and Viral Proteins", by Craig A. Smith, et al., Science 248: 1019–1023, 1990.

"Expression Cloning of a Receptor for Human Granulocyte–Macrophage Colony–Stimulating Factor" by David P. Gearing, et al., Embo J. 8(12): 3667–3676, 1989.

"The For Receptor of Natural Killer Cells is a Phospholipid Linked Membrane Protein", by David Simmons, et al., Nature 333: 568–570, 1988.

"Molecular Cloning of a CD28 cDNA by a High–Efficiency COS cell Expression System", vol. 84, by Alejandro Aruffo, et al., Proc. Natl. Acad. Sci. 84:8573–8577, 1987.

"An LFA–3 cDNA encodes a Phospholipid–linked Membrane Protein Homologous to Its Receptor CD2" by Brian Seed, Nature 329 (29):840–842, 1987.

*Primary Examiner*—Mary E. Mosher
*Assistant Examiner*—Donna C. Wortman
*Attorney, Agent, or Firm*—Finnegan, Henderson, Farabow, Garrett & Dunner, L.L.P.

[57] ABSTRACT

The invention relates to cell-free receptor binding assays which permit the binding behavior of receptor proteins in the cell membrane toward natural or artificial ligands to be investigated. This entails the particular receptor being linked to a suitable carrier molecule, preferably the heavy chain of an immunoglobulin, and being bound via the carrier, with retention of its biological property, to a suitable solid phase.

26 Claims, 15 Drawing Sheets

COMPETITION BY LIGANDS

COMPETITION BY SOLUBLE RECEPTORS

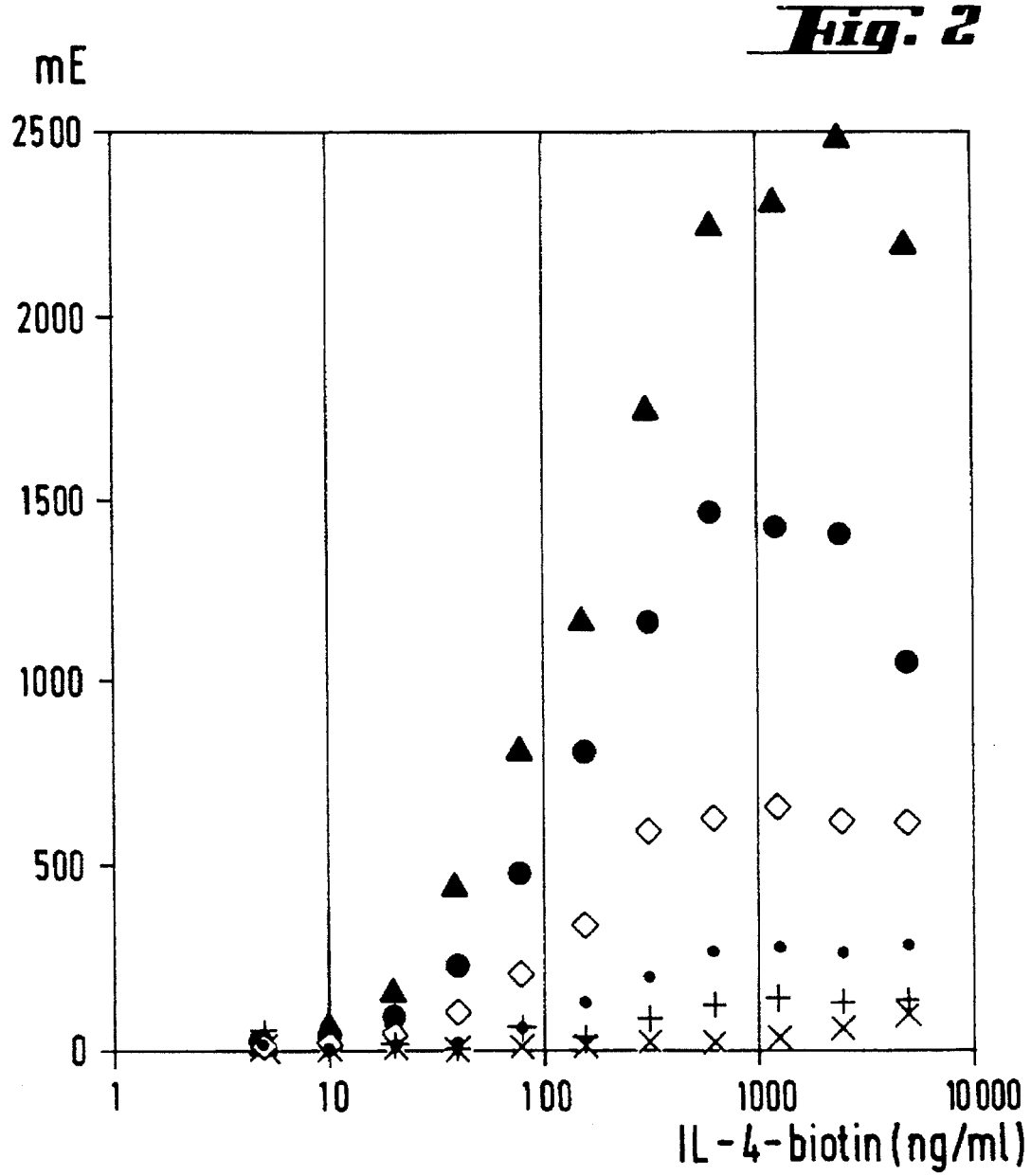

PRIMARY STRUCTURE OF TNFRFc

```
  1  MAPVAVWAAL AVGLELWAAA HALPAQVAFT PYAPEPGSTC RLREYYDQTA
     |-----------------------------------------------------

51  QMCCSKCSPG QHAKVFCTKT SDTVCDSCED STYTQLWNWV PECLSCGSRC
     --------------human TNF receptor-----------------------

101  SSDQVETQAC TREQNRICTC RPGWYCALSK QEGCRLCAPL RKCRPGFGVA
     ----------------(extracellular)------------------------

151  RPGTETSDVV CKPCAPGTFS NTTSSTDICR PHQICNVVAI PGNASMDAVC
     -------------------------------------------------------

201  TSTSPTRSMA PGAVHLPQPV STRSQHTQPT PEPSTAPSTS FLLPMGPSPP
     -------------------------------------------------------

251  AEDPEEPKSC DKTHTCPPCP APELLGGPSV FLFPPKPKDT LMISRTPEVT
     -||-linker and hinge|  |-------------------------------

301  CVVVDVSHED PEVKFNWYVD GVEVHNAKTK PREEQYNSTY RVVSVLTVLH
     ---------------------------CH2-------------------------

351  QWLNGKEYKC KVSNKALPAP IEKTISKAKG QPREPQVYTL PPSRDELTKN
     ------------------------------||-----------------------

401  QVSLTCLVKG FYPSDIAVEW ESNGQPENNY KTTPPVLDSD GSFFLYSKLT
     ---------------------------CH3-------------------------

451  VDKSRWQQGN VFSCSVMHEA LHNHYTQKSL SLSPGK
     -------------------------------------
```

Fig. 6

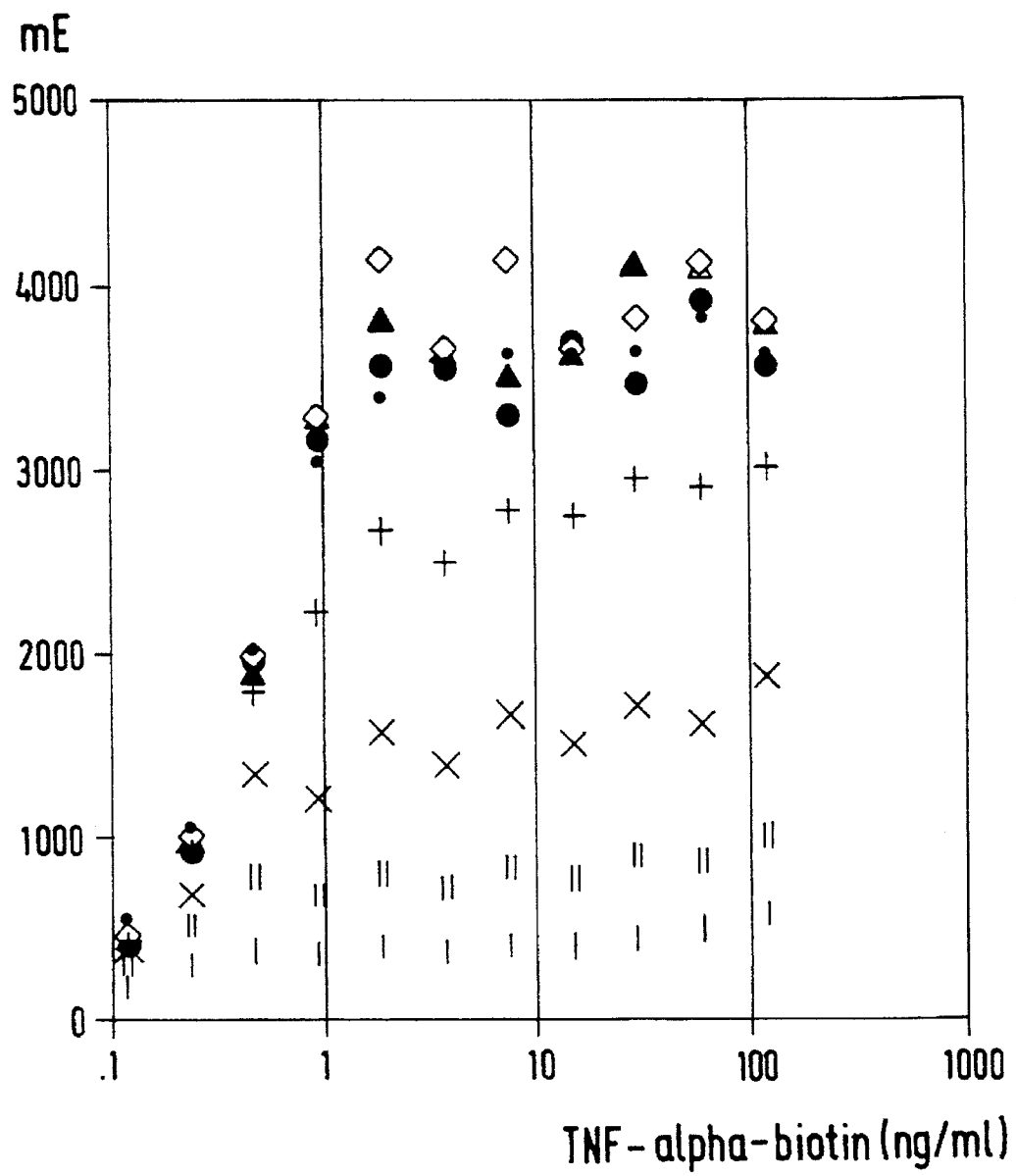

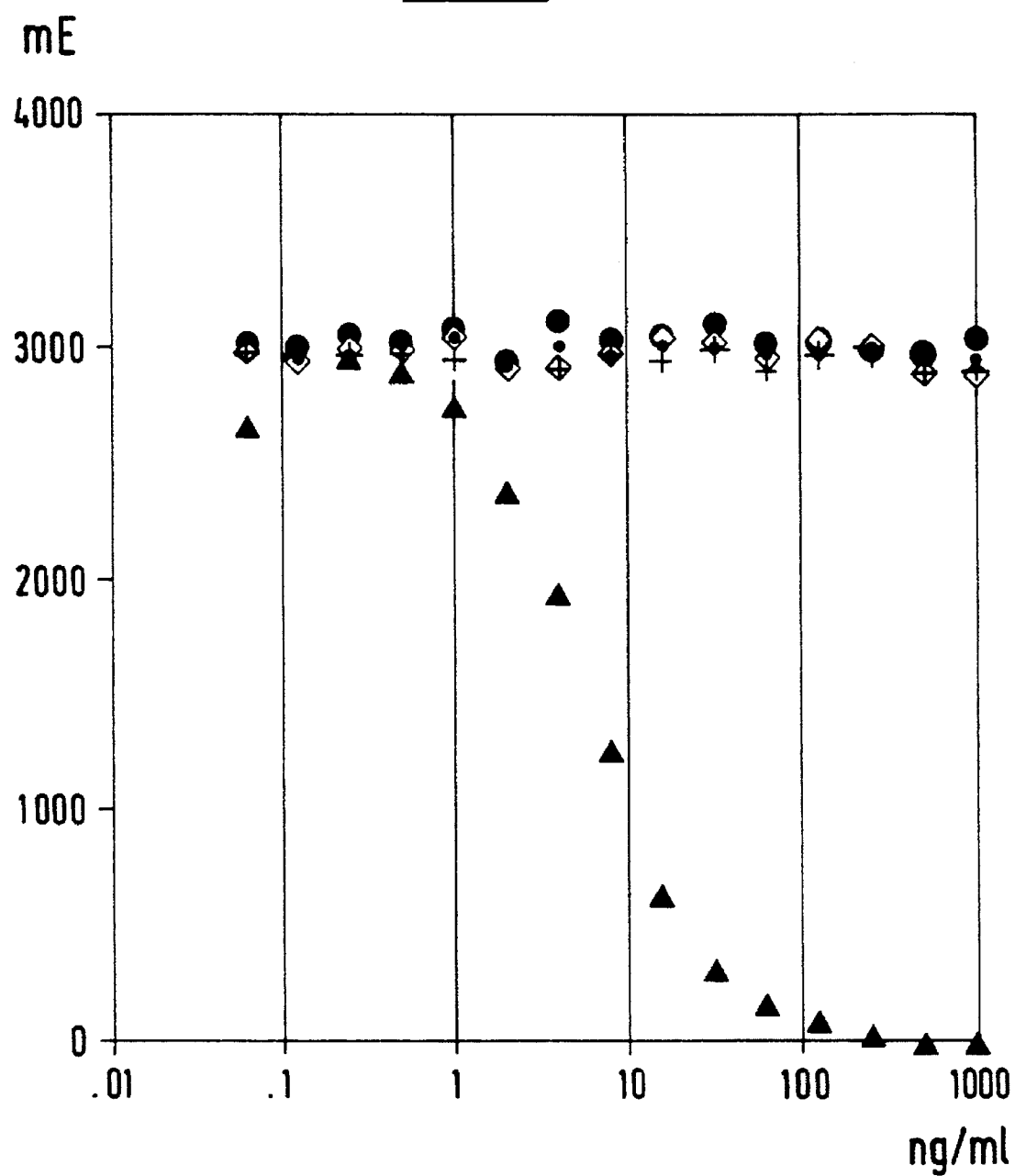

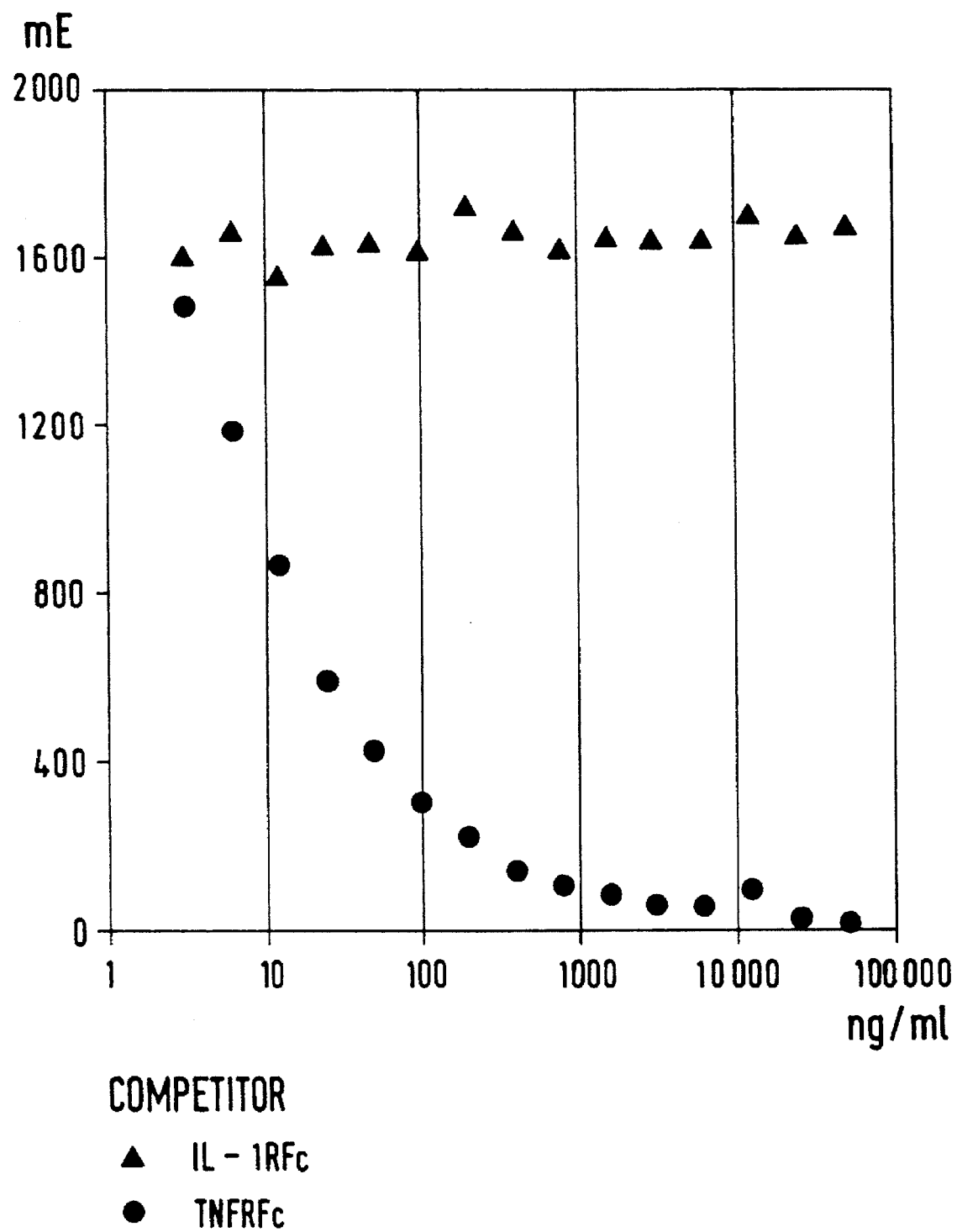

PRIMARY STRUCTURE OF GM-CSFRFc

```
  1  MLLLVTSLLL CELPHPAFLL IPEKSDLRTV APASSLNVRF DSRTMNLSWD
     |-------------------------------------------------------

51  CQENTTFSKC FLTDKKNRVV EPRLSNNECS CTFREICLHE GVTFEVHVNT
     ----------human GM-CSF receptor------------------------

101  SQRGFQQKLL YPNSGREGTA AQNFSCFIYN ADLMNCTWAR GPTAPRDVQY
     ----------------(extracellular)------------------------

151  FLYIRNSKRR REIRCPYYIQ DSGTHVGCHL DNLSGLTSRN YFLVNGTSRE
     -------------------------------------------------------

201  IGIQFFDSLL DTKKIERFNP PSNVTVRCNT THCLVRWKQP STYQKLSYLD
     -------------------------------------------------------

251  FQYQLDVHRK NTQPGTENLL INVSGDLENR YNFPSSEPRA KHSVKIRAAD
     -------------------------------------------------------

301  VRILNWSSWS EAIEFGSEDP EEPKSCDKTH TCPPCPAPEL LGGPSVFLFP
     ------------------||-linker and hinge-||---------------

351  PKPKDTLMIS RTPEVTCVVV DVSHEDPEVK FNWYVDGVEV HNAKTKPREE
     ---------------------------CH2-------------------------

401  QYNSTYRVVS VLTVLHQWLN GKEYKCKVSN KALPAPIEKT ISKAKGQPRE
     --------------------------------------------------||---

451  PQVYTLPPSR DELTKNQVSL TCLVKGFYPS DIAVEWESNG QPENNYKTTP
     ---------------------------CH3-------------------------

501  PVLDSDGSFF LYSKLTVDKS RWQQGNVFSC SVMHEALHNH YTQKSLSLSP
     -------------------------------------------------------

551  GK
     --
```

Fig. 12

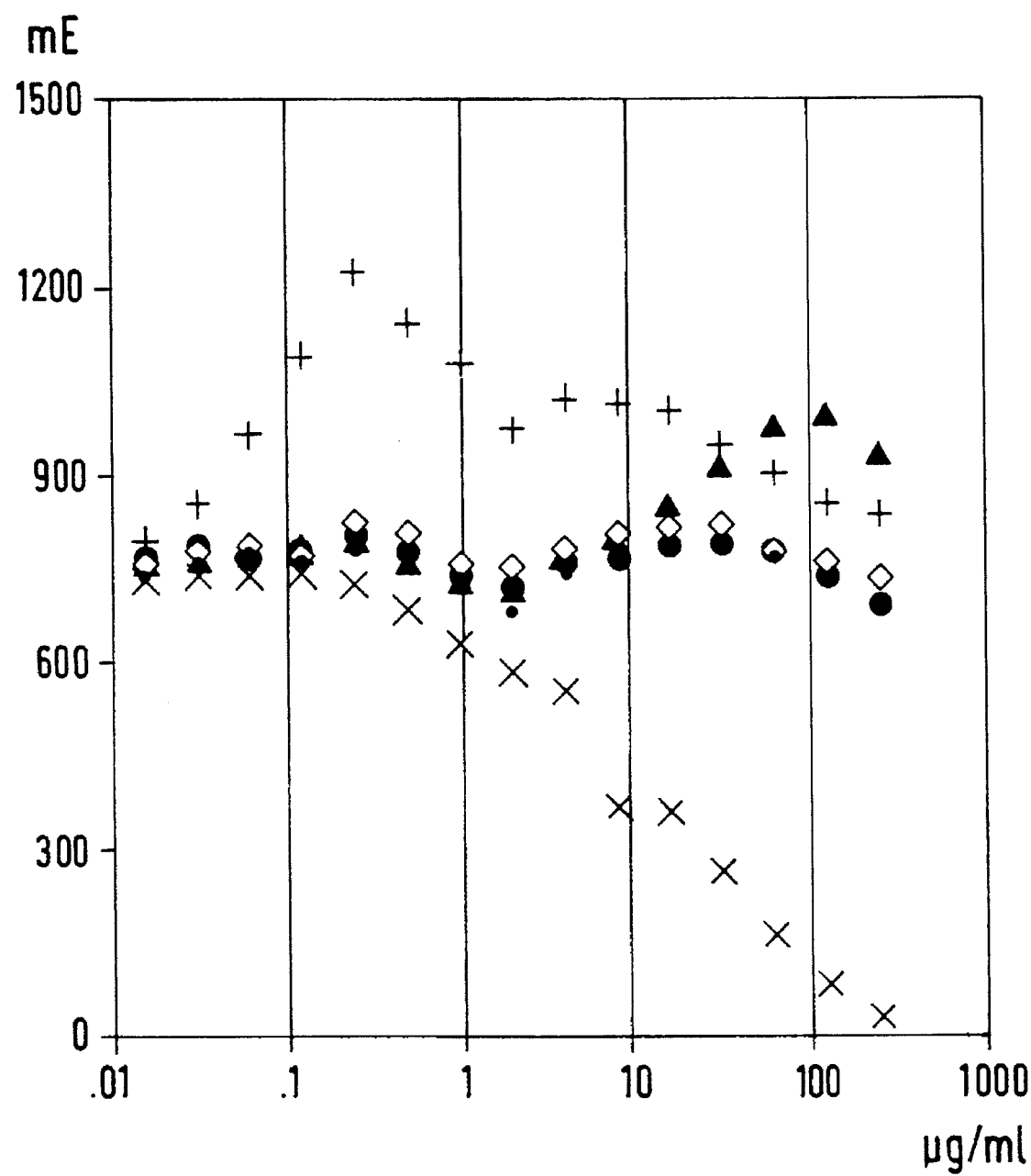

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
    ( A ) LENGTH: 486 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:1:

```
Met Ala Pro Val Ala Val Trp Ala Ala Leu Ala Val Gly Leu Glu Leu
 1               5                  10                  15

Trp Ala Ala Ala His Ala Leu Pro Ala Gln Val Ala Phe Thr Pro Tyr
                20                  25                  30

Ala Pro Glu Pro Gly Ser Thr Cys Arg Leu Arg Glu Tyr Tyr Asp Gln
            35                  40                  45

Thr Ala Gln Met Cys Cys Ser Lys Cys Ser Pro Gly Gln His Ala Lys
        50                  55                  60

Val Phe Cys Thr Lys Thr Ser Asp Thr Val Cys Asp Ser Cys Glu Asp
 65                  70                  75                  80

Ser Thr Tyr Thr Gln Leu Trp Asn Trp Val Pro Glu Cys Leu Ser Cys
                85                  90                  95

Gly Ser Arg Cys Ser Ser Asp Gln Val Glu Thr Gln Ala Cys Thr Arg
                100                 105                 110

Glu Gln Asn Arg Ile Cys Thr Cys Arg Pro Gly Trp Tyr Cys Ala Leu
            115                 120                 125

Ser Lys Gln Glu Gly Cys Arg Leu Cys Ala Pro Leu Arg Lys Cys Arg
        130                 135                 140

Pro Gly Phe Gly Val Ala Arg Pro Gly Thr Glu Thr Ser Asp Val Val
145                 150                 155                 160

Cys Lys Pro Cys Ala Pro Gly Thr Phe Ser Asn Thr Thr Ser Ser Thr
                165                 170                 175

Asp Ile Cys Arg Pro His Gln Ile Cys Asn Val Val Ala Ile Pro Gly
            180                 185                 190

Asn Ala Ser Met Asp Ala Val Cys Thr Ser Thr Ser Pro Thr Arg Ser
        195                 200                 205

Met Ala Pro Gly Ala Val His Leu Pro Gln Pro Val Ser Thr Arg Ser
    210                 215                 220
```

```
Gln  His  Thr  Gln  Pro  Thr  Pro  Glu  Pro  Ser  Thr  Ala  Pro  Ser  Thr  Ser
225                      230                     235                     240

Phe  Leu  Leu  Pro  Met  Gly  Pro  Ser  Pro  Pro  Ala  Glu  Asp  Pro  Glu  Glu
               245                      250                     255

Pro  Lys  Ser  Cys  Asp  Lys  Thr  His  Thr  Cys  Pro  Pro  Cys  Pro  Ala  Pro
               260                     265                     270

Glu  Leu  Leu  Gly  Gly  Pro  Ser  Val  Phe  Leu  Phe  Pro  Pro  Lys  Pro  Lys
          275                     280                     285

Asp  Thr  Leu  Met  Ile  Ser  Arg  Thr  Pro  Glu  Val  Thr  Cys  Val  Val  Val
     290                     295                     300

Asp  Val  Ser  His  Glu  Asp  Pro  Glu  Val  Lys  Phe  Asn  Trp  Tyr  Val  Asp
305                      310                     315                     320

Gly  Val  Glu  Val  His  Asn  Ala  Lys  Thr  Lys  Pro  Arg  Glu  Glu  Gln  Tyr
                    325                     330                     335

Asn  Ser  Thr  Tyr  Arg  Val  Val  Ser  Val  Leu  Thr  Val  Leu  His  Gln  Trp
                    340                     345                     350

Leu  Asn  Gly  Lys  Glu  Tyr  Lys  Cys  Lys  Val  Ser  Asn  Lys  Ala  Leu  Pro
               355                     360                     365

Ala  Pro  Ile  Glu  Lys  Thr  Ile  Ser  Lys  Ala  Lys  Gly  Gln  Pro  Arg  Glu
370                           375                     380

Pro  Gln  Val  Tyr  Thr  Leu  Pro  Pro  Ser  Arg  Asp  Glu  Leu  Thr  Lys  Asn
385                      390                     395                     400

Gln  Val  Ser  Leu  Thr  Cys  Leu  Val  Lys  Gly  Phe  Tyr  Pro  Ser  Asp  Ile
               405                     410                     415

Ala  Val  Glu  Trp  Glu  Ser  Asn  Gly  Gln  Pro  Glu  Asn  Asn  Tyr  Lys  Thr
               420                     425                     430

Thr  Pro  Pro  Val  Leu  Asp  Ser  Asp  Gly  Ser  Phe  Phe  Leu  Tyr  Ser  Lys
          435                     440                     445

Leu  Thr  Val  Asp  Lys  Ser  Arg  Trp  Gln  Gln  Gly  Asn  Val  Phe  Ser  Cys
     450                     455                     460

Ser  Val  Met  His  Glu  Ala  Leu  His  Asn  His  Tyr  Thr  Gln  Lys  Ser  Leu
465                      470                     475                     480

Ser  Leu  Ser  Pro  Gly  Lys
               485
```

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGCAGGTGGA AGGAGAGGAA GCGG           24

( 2 ) INFORMATION FOR SEQ ID NO:3:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AAGAATGGGA ACAGGCAGGC CTGGGC    26

( 2 ) INFORMATION FOR SEQ ID NO:4:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GATCGATTAA GCTTAGCAGG TGGAAGGAGA GGAAGCGGAT GCCG    44

( 2 ) INFORMATION FOR SEQ ID NO:5:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCCATTGAAT TTGGTTCTGA GGATCCAGAT ATGC    34

( 2 ) INFORMATION FOR SEQ ID NO:6:

( i ) SEQUENCE CHARACTERISTICS:
        ( A ) LENGTH: 552 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Met Leu Leu Leu Val Thr Ser Leu Leu Leu Cys Glu Leu Pro His Pro
 1               5                  10                  15

Ala Phe Leu Leu Ile Pro Glu Lys Ser Asp Leu Arg Thr Val Ala Pro
                20                  25                  30

Ala Ser Ser Leu Asn Val Arg Phe Asp Ser Arg Thr Met Asn Leu Ser
            35                  40                  45

Trp Asp Cys Gln Glu Asn Thr Thr Phe Ser Lys Cys Phe Leu Thr Asp
        50                  55                  60

Lys Lys Asn Arg Val Val Glu Pro Arg Leu Ser Asn Asn Glu Cys Ser
65                  70                  75                  80

Cys Thr Phe Arg Glu Ile Cys Leu His Glu Gly Val Thr Phe Glu Val
                85                  90                  95

His Val Asn Thr Ser Gln Arg Gly Phe Gln Gln Lys Leu Leu Tyr Pro
                100                 105                 110

Asn Ser Gly Arg Glu Gly Thr Ala Ala Gln Asn Phe Ser Cys Phe Ile
            115                 120                 125

Tyr Asn Ala Asp Leu Met Asn Cys Thr Trp Ala Arg Gly Pro Thr Ala
    130                 135                 140

Pro Arg Asp Val Gln Tyr Phe Leu Tyr Ile Arg Asn Ser Lys Arg Arg
145                 150                 155                 160

Arg Glu Ile Arg Cys Pro Tyr Tyr Ile Gln Asp Ser Gly Thr His Val
                165                 170                 175

Gly Cys His Leu Asp Asn Leu Ser Gly Leu Thr Ser Arg Asn Tyr Phe
                180                 185                 190
```

| | | | | | | | | | | | | | | |
|---|---|---|---|---|---|---|---|---|---|---|---|---|---|---|
| Leu | Val | Asn 195 | Gly | Thr | Ser | Arg | Glu 200 | Ile | Gly | Ile | Gln | Phe 205 | Asp | Ser |
| Leu | Leu 210 | Asp | Thr | Lys | Lys | Ile 215 | Glu | Arg | Phe | Asn | Pro 220 | Pro | Ser | Asn | Val |
| Thr 225 | Val | Arg | Cys | Asn | Thr 230 | Thr | His | Cys | Leu | Val | Arg 235 | Trp | Lys | Gln | Pro 240 |
| Ser | Thr | Tyr | Gln | Lys 245 | Leu | Ser | Tyr | Leu | Asp 250 | Phe | Gln | Tyr | Gln | Leu 255 | Asp |
| Val | His | Arg | Lys 260 | Asn | Thr | Gln | Pro | Gly 265 | Thr | Glu | Asn | Leu | Leu 270 | Ile | Asn |
| Val | Ser | Gly 275 | Asp | Leu | Glu | Asn | Arg 280 | Tyr | Asn | Phe | Pro | Ser 285 | Ser | Glu | Pro |
| Arg | Ala 290 | Lys | His | Ser | Val | Lys 295 | Ile | Arg | Ala | Ala | Asp 300 | Val | Arg | Ile | Leu |
| Asn 305 | Trp | Ser | Ser | Trp | Ser 310 | Glu | Ala | Ile | Glu | Phe 315 | Gly | Ser | Glu | Asp | Pro 320 |
| Glu | Glu | Pro | Lys | Ser 325 | Cys | Asp | Lys | Thr | His 330 | Thr | Cys | Pro | Pro | Cys 335 | Pro |
| Ala | Pro | Glu | Leu 340 | Leu | Gly | Gly | Pro | Ser 345 | Val | Phe | Leu | Phe | Pro 350 | Pro | Lys |
| Pro | Lys | Asp 355 | Thr | Leu | Met | Ile | Ser 360 | Arg | Thr | Pro | Glu | Val 365 | Thr | Cys | Val |
| Val | Val 370 | Asp | Val | Ser | His | Glu 375 | Asp | Pro | Glu | Val | Lys 380 | Phe | Asn | Trp | Tyr |
| Val 385 | Asp | Gly | Val | Glu | Val 390 | His | Asn | Ala | Lys | Thr 395 | Lys | Pro | Arg | Glu | Glu 400 |
| Gln | Tyr | Asn | Ser | Thr 405 | Tyr | Arg | Val | Val | Ser 410 | Val | Leu | Thr | Val | Leu 415 | His |
| Gln | Trp | Leu | Asn 420 | Gly | Lys | Glu | Tyr | Lys 425 | Cys | Lys | Val | Ser | Asn 430 | Lys | Ala |
| Leu | Pro | Ala 435 | Pro | Ile | Glu | Lys | Thr 440 | Ile | Ser | Lys | Ala | Lys 445 | Gly | Gln | Pro |
| Arg | Glu 450 | Pro | Gln | Val | Tyr | Thr 455 | Leu | Pro | Pro | Ser | Arg 460 | Asp | Glu | Leu | Thr |
| Lys 465 | Asn | Gln | Val | Ser | Leu 470 | Thr | Cys | Leu | Val | Lys 475 | Gly | Phe | Tyr | Pro | Ser 480 |
| Asp | Ile | Ala | Val | Glu 485 | Trp | Glu | Ser | Asn | Gly 490 | Gln | Pro | Glu | Asn | Asn 495 | Tyr |
| Lys | Thr | Thr | Pro 500 | Pro | Val | Leu | Asp | Ser 505 | Asp | Gly | Ser | Phe | Phe 510 | Leu | Tyr |
| Ser | Lys | Leu 515 | Thr | Val | Asp | Lys | Ser 520 | Arg | Trp | Gln | Gln | Gly 525 | Asn | Val | Phe |
| Ser | Cys 530 | Ser | Val | Met | His | Glu 535 | Ala | Leu | His | Asn | His 540 | Tyr | Thr | Gln | Lys |
| Ser 545 | Leu | Ser | Leu | Ser | Pro 550 | Gly | Lys | | | | | | | | |

CELL-FREE RECEPTOR BINDING ASSAYS, THE PRODUCTION AND USE THEREOF

This application is a continuation of application Ser. No. 08/110,798 filed Aug. 23, 1993, now abandoned, which was a continuation application of Ser. No. 07/798,564 filed Nov. 26, 1991, now abandoned.

The invention relates to cell-free receptor binding assays which permit the binding behavior of receptor proteins in the cell membrane toward natural or artificial ligands to be investigated. This entails the particular receptor being linked to a suitable carrier molecule, preferably the heavy chain of an immunoglobulin, and being bound via the carrier, with retention of its biological property, to a suitable solid phase.

Determination of the binding behavior of receptor proteins in the cell membrane toward natural or artificial ligands is important for many biological and medical studies. It is usual for this purpose to radiolabel a ligand and determine its specific binding by suitable methods such as equilibrium centrifugation, equilibrium dialysis or filtration. The receptor molecules may in this instance remain bound to the cell, in which case the assay is carried out with whole cells, but may also be present in subcellular fractions such as membrane vesicles or else extracted from the cell membrane with suitable detergents and stabilized in detergent micelles. The said receptor binding assays are increasingly difficult to carry out as the number of receptor molecules in the cell membrane decreases. Many receptors, especially including those of great medical interest, are normally expressed on the cell surface to only a small extent (of the order of a few hundred to a few thousand molecules per cell). These include, for example, the receptors for granulocyte/macrophage colony-stimulating factor (GM-CSF), many interleukins, erythropoietin, tumor necrosis factor (TNF) etc.

The preferred aim of the present invention was to develop suitable binding assays for, preferably, receptors of these types. A specific, sensitive and easily performed binding assay for these and other receptors would make it possible, for example, to assay a large number of compounds for their binding properties, in order in this way to identify candidate agonists or antagonists ("receptor screening"). Furthermore, it might be possible with such assays also to test antibodies directed against receptors or ligands to find whether they are directed against epitopes which play a part in the binding. The object according to the invention was to produce an assay system of this type. EP-A 0325 262, EP-A 0314 317 and German Patent Application (DE) P 4020 607.6 disclose or propose fusion proteins composed of various portions of the extracellular domains of human membrane proteins or soluble proteins (fusion partners) and the constant part (Fc) of the heavy chain of an Ig. This entails, at the DNA level, the coding sequence of the fusion partner being fused with a DNA coding for the Fc part in such a way that the fusion partner preferably contributes the amino-terminal portion of the fusion protein. The recombinant DNA is then expressed in suitable cell systems. Fusion partners for the Fc part are, on the one hand, proteins belonging to the immunoglobulin family, such as the T-cell antigen CD 4 (EP-A 0325 262 and 0314 317), and, on the other hand, structurally unrelated proteins such as tissue factor or the receptor for interleukin4 (IL4) (DE P 4020607.6). The said fusion proteins are preferably expressed in animal cells. The amino-terminal fusion partner usually retains its biological activity; for example, if it is derived from a normally membrane-bound receptor protein, it binds ligands with an affinity equivalent to that of the membrane-bound receptor. Thus, if a receptor protein is characterized on the cDNA level, it is possible in principle to produce large quantities of biologically active molecules in recombinant expression systems. These can then be employed, as described below, in a binding assay. In animal cells, the described fusion proteins are secreted and can easily be purified from the culture supernatant by affinity chromatography, because they bind via their Fc part to protein A which in turn can be coupled to, for example, Sepharose. The fusion proteins can also be synthesized in known prokaryotic expression systems (*E. coli*, Pseudomonas, Bacillus etc.) or yeasts (for example *Saccharomyces cerevisiae*) using known, suitable expression vectors. Besides the Fc part which is described and preferred for the invention (carrier), it is also possible according to the invention for fusion partners to be coupled to any other carrier proteins (for example albumin, protein A, protein G, glutathione S-transferase, *Staphylococcus aureus* nuclease).

To carry out the receptor binding assays according to the invention, initially an antiserum (or monoclonal antibody) directed against the carrier part, or another suitable agent, is used to coat a solid phase, for example an ELISA plate. Since the Fc part of an antibody is preferably employed, and the Fc part of a human IgG1 is particularly preferably employed, as carrier, it is preferable to use a rabbit serum specifically directed against the CH2 domain of a human IgG1. The fusion proteins are then bound via their carrier part to the previously coated solid phase.

Figure 1B:
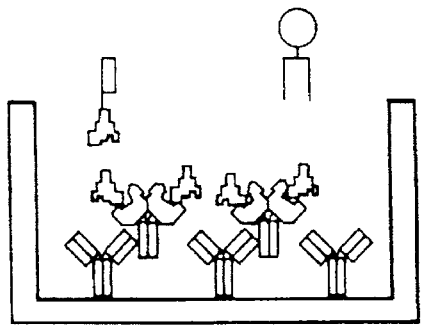
Figure 1C:
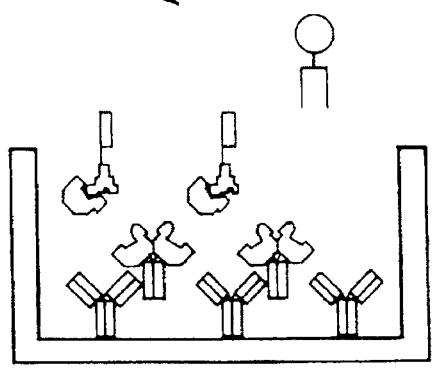

This means that the binding sites located on the receptor portion remain accessible to ligands. In order now to be able to detect the bound ligand, it is necessary for it to be labelled. This can take place, for example, by introducing a radioactive nuclide (for example Siekierka, J. J. and DeGudicibus, S., Anal. Biochem. Vol. 172 (1988), 514–517), but preferably by biotinylation of the ligand (King and Catino, Anal. Biochem. Vol. 188 (1990), 97–100). The latter is then in turn detected by a streptavidin-enzyme conjugate, preferably streptavidin-peroxidase. The principle of the design of the assays according to the invention is depicted byway of example in FIG. 1A to FIG. 1C.

The possible uses of the assays according to the invention are wide, and those preferred are listed below and likewise form part of the invention:

Use in "receptor screening":
  a) Receptor in the solid phase: screening of a large number of substances to identify agonists and antagonists of the ligand.
  b) Ligand in the solid phase: screening of a large number of substances to identify agonists and antagonists of the receptor.

Use in antibody screening: Identification of antibodies which influence the interaction between ligand and receptor.

Use for the quantitative detection of the binding activity of soluble receptor forms.

Use for the quantitative determination of the biological activity of specific ligands.

Functional analysis of modified ligands ("muteins") or parts (for example oligopeptides) thereof.

Identification of substances which influence the interaction of pathogenic organisms (for example viruses or bacteria) with their cellular receptors.

Identification of substances which influence the interaction of cellular adhesion molecules.

The invention is furthermore explained in detail in the examples and contained in the patent claims.

EXAMPLE 1

Cell-free IL-4 binding assay

Figure 3:
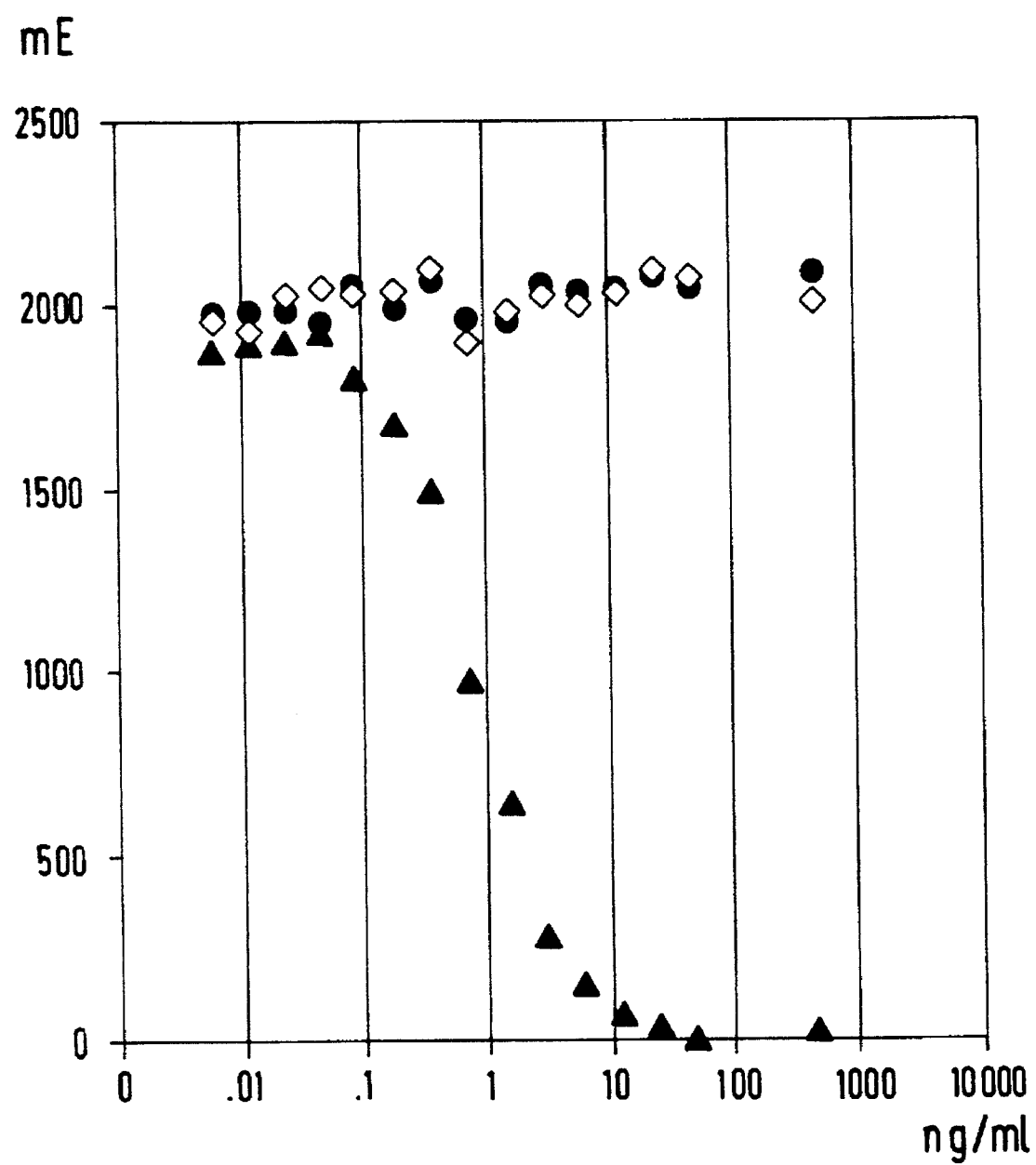

DE P 4020 607.6 discloses the protein IL-4RFc. It is composed of the extracellular portion of the human receptor for IL-4 which is fused to the Fc part of the heavy chain of a human IgG1 molecule. ELISA plates (Nunc, type B) were coated overnight at 4° C. with 100 µl of an affinity-purified rabbit serum against the CH2 domain of human IgG (Dakopatts). The concentration was 10 µg/ml in PBS (137 mM NaCl, 2.7 mM KCl, 6.1 mM $Na_2HPO_4$, 3.9 mM $KH_2PO_4$, 0.5 mM $MgCl_2$, 0.1 mM $CaCl_2$, pH 7.0). The assay plate was washed five times with PBS containing 0.05% Tween 20 and then incubated with 275 µl of PBS containing 5% skim milk powder at room temperature for 60 min and then washed as above. Then a "checkerboard titration" was initially carried out in order to determine a suitable combination of receptor and ligand concentrations for the design of the assay. To do this, the assay plate was initially incubated with various concentrations of purified IL-4RFc protein (100 µl) in Eagle's medium (Dulbecco's modification) containing 10% fetal calf serum (DMEM/FCS) at room temperature for 60 min and then washed as above. IL-4 was biotinylated using N-hydroxysuccinimidobiotin (Sigma) (Niendorf, A. et al., J. Histochem. Cytochem. Vol. 34 (1986), 357–361) and bound in various concentrations in DMEM/FCS (100 µl) to the assay plate which had been preincubated with IL-4RFc, likewise at room temperature for 60 min. After washing as above, incubation with 100 µl of streptavidin-peroxidase (Amersham; 1:250 in DMEM/FCS) was carried out at room temperature for 30 min and then washed as above. The bound peroxidase was detected by the color produced in 100 µl of tetramethylbenzidine substrate solution (Behringwerke). After incubation at room temperature for 30 min, the extinction at 450 nm was measured. The results of the test are depicted in FIG. 2. A number of typical binding plots is obtained, depending on the amounts of receptor and ligand employed. The signal which reflects the bound ligand reaches a plateau at a height which increases with the amount of receptor employed to coat the assay plate. Further tests with the competition assays depicted diagrammatically in FIG. 1 made use of a combination of 300 ng/ml IL-4RFc for coating and 300 ng/ml IL-4-biotin for binding. To calculate the concentration of IL-4-biotin as well as of the ligands listed in Examples 3 and 5, it was assumed that all the ligand employed for the biotinylation was actually recovered. The signal (about 2000 mE) produced by the combination used is (i) clearly measurable and (ii) not yet located on the plateau for the receptor concentration used. The specificity and sensitivity of the assay were determined by investigating the extent to which various ligands are able to compete with IL-4-biotin for binding to IL-4-RFc (FIG. 3). Employed for this was a constant concentration (300 ng/ml) of IL-4-biotin in the presence of various concentrations of IL-1-alpha, of IL-3 and IL-4. FIG. 3 shows that only IL-4 is able to compete effectively, whereas IL-1-alpha and IL-3 show no binding activity in the concentrations employed. The concentration of IL-4 at which half-maximal inhibition of binding of IL-4-biotin is observed (IC50) is 1 ng/ml.

EXAMPLE 2

Detection of soluble IL-4 receptor in the cell-free binding assay

Figure 4:
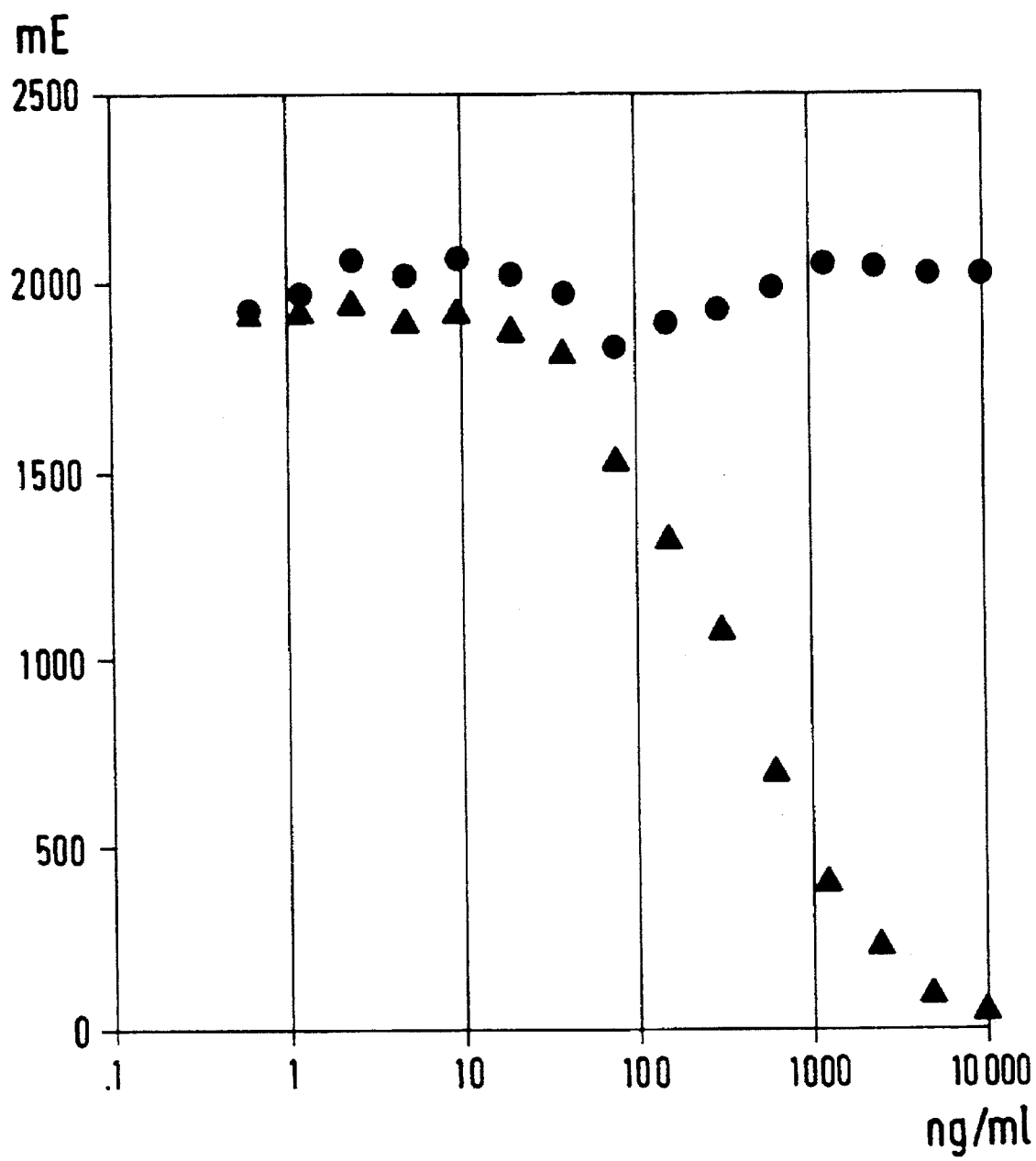

The intention was to show whether it is possible with the assay to detect not only competing ligands but also recombinant soluble forms of receptors. The IL-4RFc protein itself was chosen for this. The assay design was as described in Example 1, but free Fc binding sites remaining after incubation of the assay plate with the standard concentration of IL-4RFc (300 ng/ml) were saturated by incubation with 10% human serum in DMEM/FCS (60 min at room temperature). After this the binding assay was carried out in the presence of various concentrations of IL-4RFc. FIG. 4 shows that IL-4RFc really can be detected in this competition assay, whereas IL-7RFc, an Fc fusion of the human IL-7 receptor, shows no binding activity. The IC50 for IL-4RFc is 250 ng/ml.

EXAMPLE 3

Cell-free TNF binding assay cDNA for the 80 kD form of the human TNF receptor has recently been isolated (Smith, C. A. et al., Science, Vol. 248 (1990), 1019–1023). It codes for a typical membrane protein composed of the amino-terminal extra-cellular domain, of a transmembrane region and of a carboxy-terminal cytoplasmic domain. A unique cleavage site for the restriction enzyme PvuII is located in the coding region for the TNF receptor immediately in front of the codons for the last five amino acid residues of the extracellular region. The expression plasmid huTNFRcavnot containing the cDNA was cut with PvuII and ligated with BamHI linkers (5' CGGATCCG 3'). This was followed by cleavage with NotI which cuts immediately in front of the 5'-untranslated region of the TNF receptor. The resulting protrusion was filled in with Klenow enzyme and then a BamHI cleavage was carried out. The resulting NotI (filled-in)/BamHI fragment (~800 bp) codes for the entire extracellular domain of the TNF receptor (with the exception of the five amino-acid residues immediately in front of the transmembrane region) with a continuous reading frame from the initiation codon to the nucleotide sequence GAT which is contained in the BamHI recognition sequence and which, in this reading frame, codes for an aspartic acid residue. This fragment was cloned into the vector p4EGammaH which is disclosed in DE P 4020607.6. To do this, p4EGammaH was cut with HindIII and, after filling in the resulting protrusion using Klenow enzyme, with BamHI. The resulting expression plasmid pTNFRFc codes for the fusion protein TNFRFc (SEQ ID NO:1) from the extra-cellular portion of the TNF receptor, which is coupled via the hinge region to the Fc part of the heavy chain of a human IgG1. pTNFRFc is depicted diagrammatically in FIG. 5, and the amino-acid sequence of the TNFRFc encoded therein is depicted in FIG. 6 (SEQ ID NO:1). pTNFRFc was transfected into BHK cells, and stable clones were obtained after double selection with methotrexate and G418 (EP-A 0330 977). Typical expression rates were 20 µg/ml of supernatant, from which TNFRFc (SEQ ID NO: 1) was isolated by chromatography on protein A-Sepharose (DE P 4020607.6). TNFRFc (SEQ ID NO:1) and biotinylated TNF-alpha were initially subjected to a checkerboard titration as described in Example 1 in order to define suitable conditions for a binding assay. FIG. 7 shows a series of binding plots obtained in this test. Chosen for subsequent tests was the combination of 200 ng/ml TNFRFc (SEQ ID NO:1) for coating and 20 ng/ml TNF-alpha-biotin for binding. The TNF binding assay is also sensitive and specific for TNF-alpha. FIG. 8 depicts the result of a competition test. Only TNF-alpha inhibits binding of TNF-alpha-biotin with an IC50 of 5 ng/ml, whereas IL-1-alpha, IL-3, IL-4 and GM-CSF show no effect in the concentrations used.

EXAMPLE 4

Detection of soluble TNF receptor in the cell-free binding assay

This test was carried out in analogy to that described in Example 2 (FIG. 9). TNFRFc (SEQ ID NO:1) inhibits with an IC50 of 35 ng/ml, whereas IL-1RFc, a fusion protein composed of the human IL-1 receptor and the Fc part of a human IgG1, does not inhibit.

EXAMPLE 5

Figure 10:
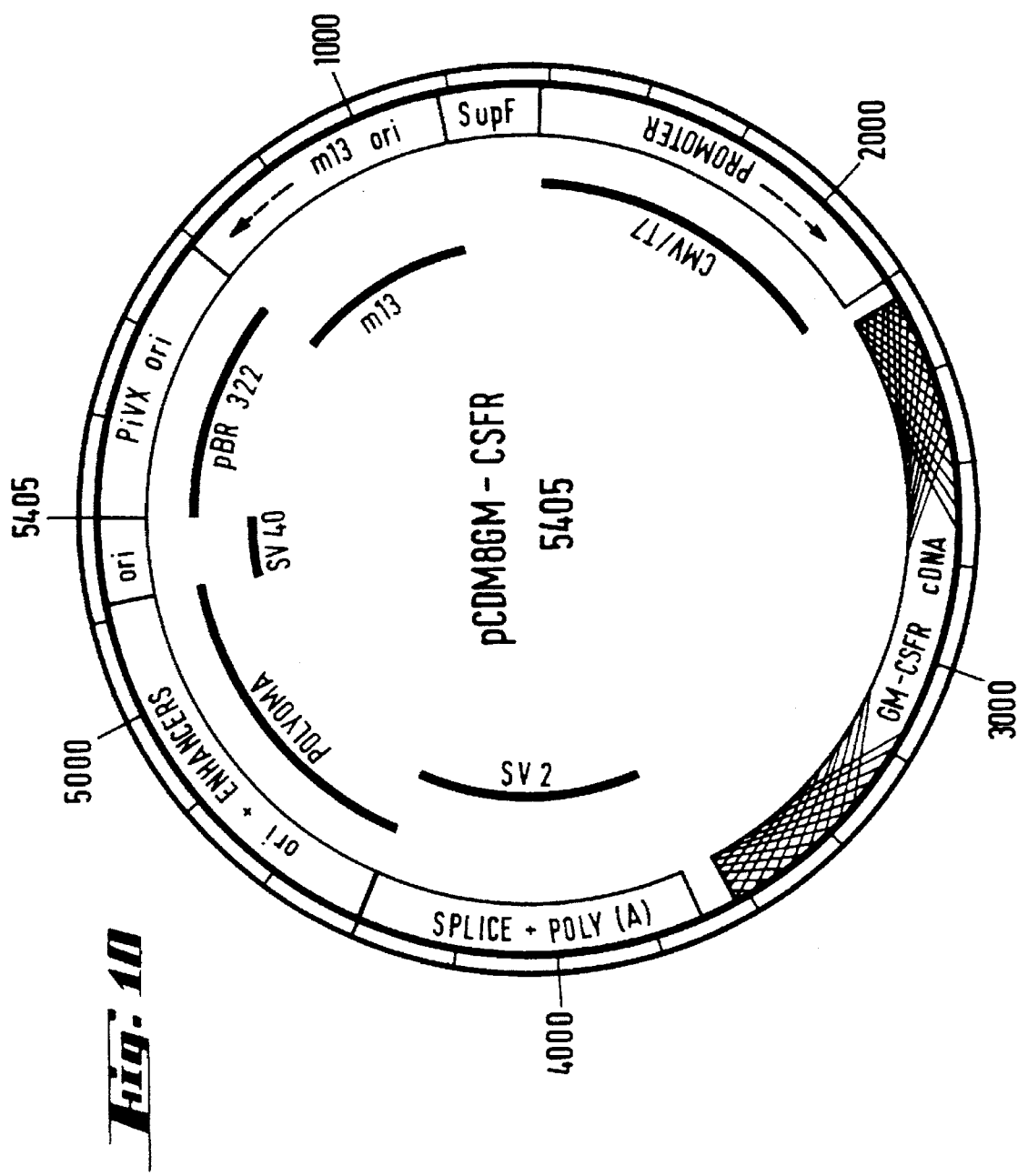

Cell-free GM-CSF binding assay cDNA for a human receptor for GM-CSF has been isolated (Gearing, D. P. et al., EMBO J. Vol. 8 (1989), 3667–3676). The GM-CSF receptor is also a typical membrane protein with amino-terminal extracellular domain, transmembrane region and carboxy-terminal intracellular domain. Two oligonucleotides able to hybridize with regions in the 5'-untranslated region (oligonucleotide A: 5'AGCAG-GTGGAAGGAGAGGAAGCGG 3') (SEQ ID NO:2) and 3'-untranslated region (oligonucleotide B: 5'AAGAATGG-GAACAGGCAGGCCTGGGC 3') (SEQ ID NO:3) respectively are synthesized. Amplification of the plasmid DNA from a human placental cDNA gene bank (Simmons, D. and Seed, B., Nature, Vol. 333 (1988), 568–570) with thermostable Taq DNA polymerase yielded a DNA fragment (about 1400 bp) whose size corresponds to that of the GM-CSF receptor cDNA. Restriction analyses confirmed the identity of the amplified DNA fragment. After ligation of BstXI adapters (Aruffo, A. and Seed, B., Proc. Natl. Acad. Sci. USA, Vol. 84, 8573–8577), the fragment was inserted into the BstXI-treated eukaryotic expression vector CDM8 (Seed, B., Nature, Vol. 329 (1987), 840–842). The resulting plasmid pCDM8GM-CSFR is depicted diagrammatically in FIG. 10.

In order to be able to produce an Fc fusion with GM-CSF receptor, renewed DNA amplification with thermostable Taq DNA polymerase was carried out on pCDM8GM-CSFR.

Two further oligonucleotides were synthesized to do this. Oligonucleotide

Figure 11:
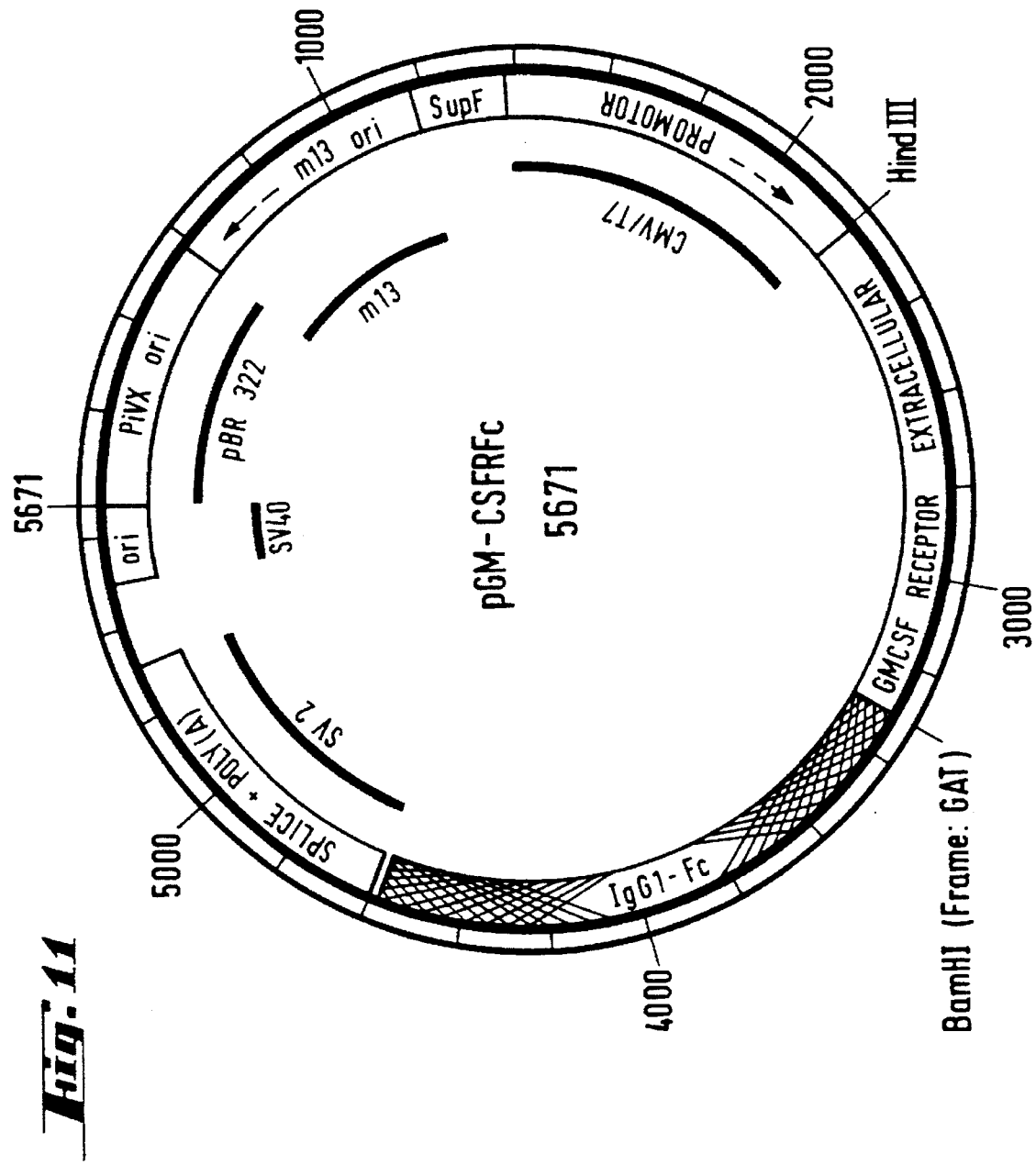

C    (5' GATCGATTAAGCTTAGCAGGTGGAAGGAGAGGAAGCGGATGCCG 3')

hybridizes (SEQ ID NO:4) with the 5'-untranslated region and inserts a HindIII cleavage site in front of the latter, oligonucleotide D (5'GCCATTGAATTTGGTTCTGAGGATCCAGATATGC 3') hybridizes (SEQ ID NO:5) with the cDNA in front of the coding region for the transmembrane domain and inserts a BamHI cleavage site immediately in front of the latter. The expected 1131 bp fragment was obtained and, after treatment with BamHI and HindIII, inserted into the BamHI/HindIII-cut vector p4EGammaH. The expression plasmid pGM-CSFRFc generated in this way codes for the fusion protein GM-CSFRFc (SEQ ID NO:6) composed of the extracellular domain of the GM-CSF receptor which is coupled via the hinge region to the Fc part of a human IgG1. pGM-CSFRFc and the peptide sequence of the fusion protein GM-CSFRFc (SEQ ID NO:6) are depicted in FIGS. 11 and 12 respectively.

Transient expression of pGM-CSFRFc in COS cells was carried out. To do this, COS cells were transfected with pGM-CSFRFc with the aid of DEAE-dextran (EP-A 0325 262). The supernatants were used for the cell-free GM-CSF binding assay.

Figure 13:
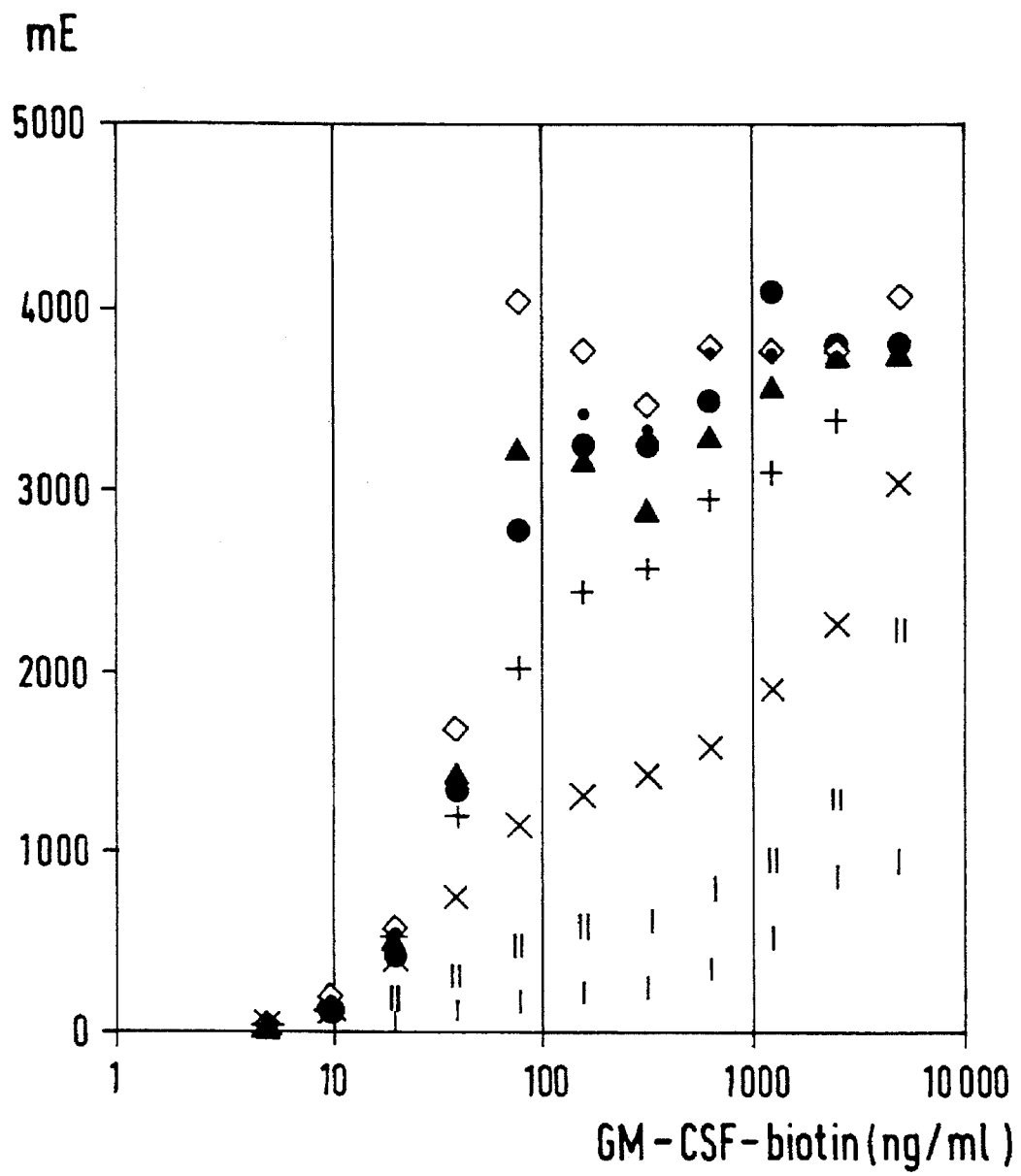

FIG. 13 shows the result of the checkerboard titration with GM-CSFRFc (SEQ ID NO:6) and biotinylated GM-CSF. Chosen for subsequent tests was the combination of 1000 ng/ml GM-CSFRFc (SEQ ID NO:6) for coating and 150 ng/ml GM-CSF-biotin for binding.

Figure 14:
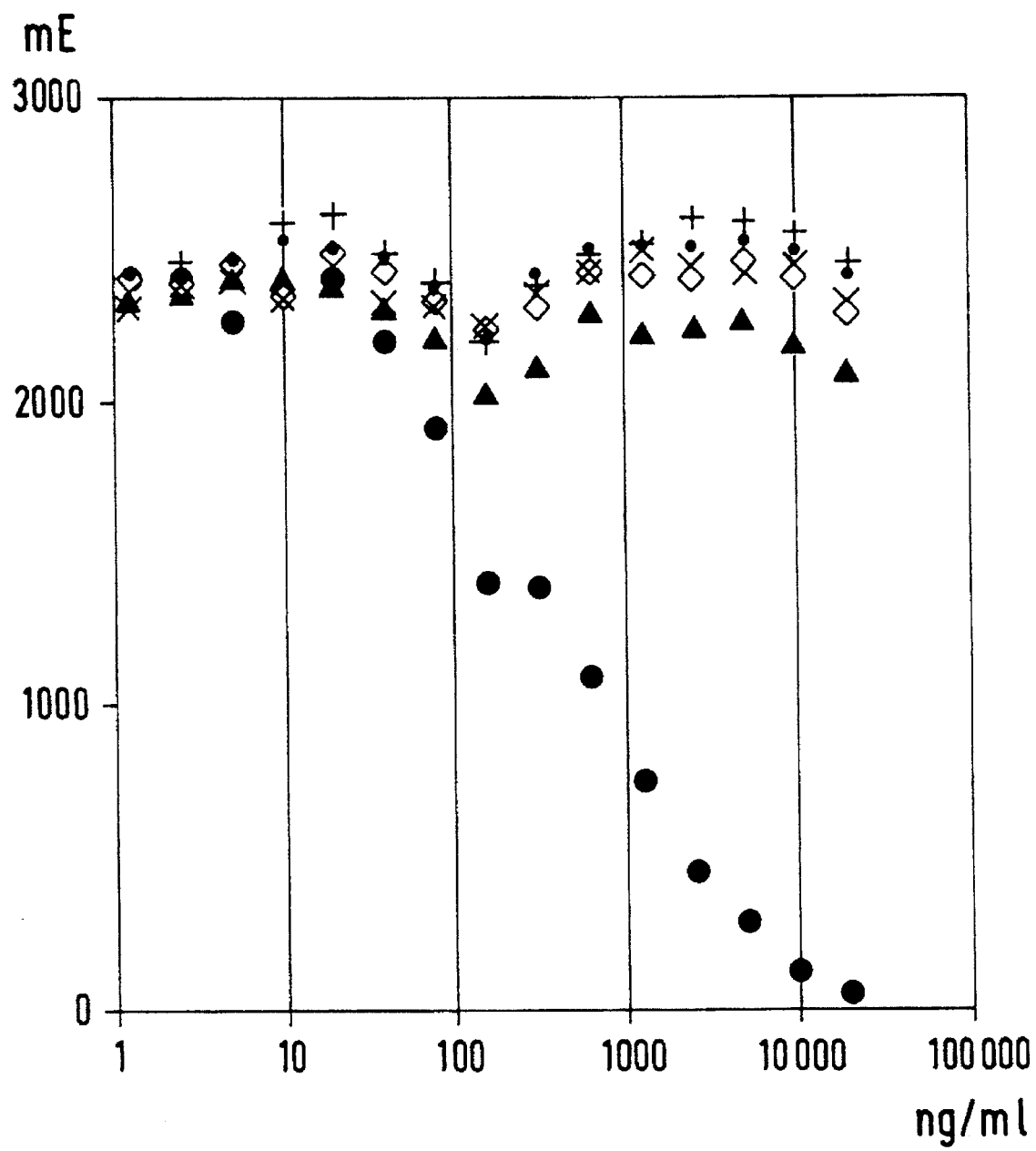

The binding assay is specific for GM-CSF. Under the chosen conditions, unlabelled GM-CSF inhibits the binding of GM-CSF-biotin with an IC50 of 200 ng/ml, whereas TNF-alpha, G-CSF, IL-1-alpha, IL-3 and IL-4 do not inhibit in the concentrations used (FIG. 14).

EXAMPLE 6

Characterization of monoclonal antibodies against GM-CSF in the cell-free receptor binding assay A number of different monoclonal antibodies against GM-CSF have been produced (Behringwerke). They were employed at the same time as GM-CSF-biotin in the binding assay under the conditions described in Example 5 (FIG. 15).

The monoclonal antibody 699/779 inhibits binding and is thus very probably directed against a receptor binding epitope on GM-CSF. The monoclonal antibodies 691/A40, 799/3, 3.G11, 932/453 and the control antibody BMA031 (directed against a human T-cell receptor) by contrast do not inhibit. 932/453 and, to a smaller extent, also 691/A40 in fact bring about an increase in the measured signal.

Key to the Figures

Key to FIG. 1:

Principle of the design of the cell-free receptor binding assay:

A) A receptor/carrier fusion protein (3) is bound via an anti-carrier antibody (4) or another suitable agent to a solid phase. A labelled ligand (2) is able to bind to the receptor binding site and in turn can be measured via a detection/amplification system (1).

B) An unlabelled ligand of the receptor can be detected via the competition for the receptor binding site.

C) Soluble receptor can be detected via the competition for the labelled ligand.

Key to FIG. 2:

Cell-free IL-4 binding assay: dependence of the IL-4-biotin binding on the IL-4RFc concentration used for coating the ELISA plate.

Key to FIG. 3:

Cell-free IL-4 binding assay:

Dependence of the IL-4-biotin binding on the concentration of the ligands employed for competition.

Key to FIG. 4:

Cell-free IL-4 binding assay:

Dependence of the IL-4-biotin binding on the concentration of the receptor/Fc fusion proteins employed for competition.

Figure 5:
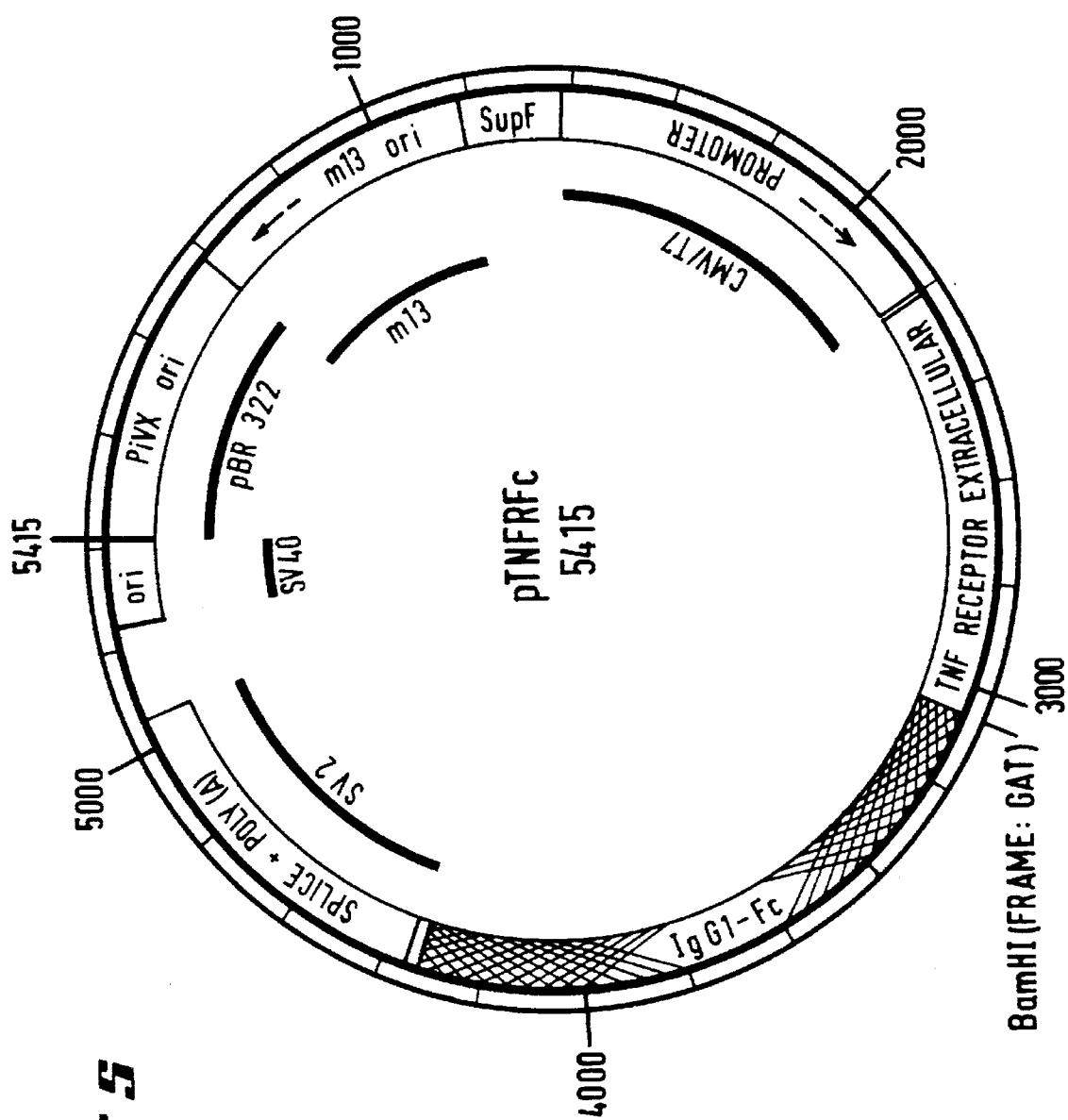

Key to FIG. 5:

Diagrammatic structure of the expression plasmid pTNFRFc.

Key to FIG. 6:

Amino-acid sequence of the fusion protein TNFRFc (SEQ ID NO:1).

Key to FIG. 7:

Cell-free TNF-alpha binding assay:

Dependence of the TNF-alpha-biotin binding on the TNFRFc concentration used for coating the ELISA plate.

Key to FIG. 8:

Cell-free TNF-alpha binding assay:
 Dependence of the TNF-alpha-biotin binding on the concentration of the ligands employed for competition.
Key to FIG. 9:
Cell-free TNF-alpha binding assay:
 Dependence of the TNF-alpha-biotin binding on the concentration of the receptor/Fc fusion proteins employed for competition.
Key to FIG. 10:
Diagrammatic structure of the expression plasmid pCDM8GM-CSFR.
Key to FIG. 11:
Diagrammatic structure of the expression plasmid pGM-CSFRFc.
Key to FIG. 12:
Amino-acid sequence of the fusion protein GM-CSFRFc (SEQ ID NO:6).
Key to FIG. 13:
Cell-free GM-CSF binding assay:
 Dependence of the GM-CSF-biotin binding on the GM-CSFRFc concentration used for coating the ELISA plate.
Key to FIG. 14:
Cell-free GM-CSF binding assay:
 Dependence of the GM-CSF-biotin binding on the concentration of the ligands employed for competition.
Key to FIG. 15:
Cell-free GM-CSF binding assay:
 Dependence of the GM-CSF-biotin binding on the concentration of the anti-GM-CSF antibodies employed in the binding assay.

We claim:

1. An article for a binding assay for investigating binding behavior of a cellular receptor protein to a labeled natural or artificial ligand comprising (1) a binding partner I which is a recombinant fusion protein comprising a cellular receptor linked to a carrier protein, wherein said carrier protein is an immunoglobin and further wherein said carrier protein is bound to a solid phase by an antiserum or monoclonal antibody thereby retaining binding activity of the receptor to a binding partner II, and (2) binding partner II which is a labeled natural or artificial ligand.

2. An article as claimed in claim 1, in which the cellular receptor in the recombinant fusion protein is a soluble protein.

3. An article as claimed in claim 1, in which the carrier protein in the recombinant fusion protein does not influence biological activity of the cellular receptor and makes the fusion protein amenable to purification by affinity chromatography.

4. An article as claimed in claim 1, in which the binding partner II is radiolabeled and can be detected.

5. An article as claimed in claim 1, in which the binding partner II is linked to a low molecule weight compound and wherein said compound is detectable.

6. An article as claimed in claim 1, in which the binding partner II is linked to an enzyme and the enzyme is detectable.

7. An article as claimed in claim 6 wherein the enzyme is peroxidase, alkaline phosphatase or luciferase.

8. An article as claimed in claim 5, further comprising a streptavidin-peroxidase conjugate.

9. An article as claimed in claim 5 wherein the low molecular weight compound is biotin.

10. An article for a binding assay for investigating binding behavior of a cellular receptor protein to a labeled natural or artificial ligand comprising
    (1) a binding partner I which is a recombinant fusion protein comprising a cellular receptor linked to a carrier protein, wherein said carrier protein is the constant part of the heavy chain of an immunoglobulin and further wherein said carrier protein is bound to a solid phase by an antiserum or monoclonal antibody thereby retaining binding activity of the receptor to a binding partner II, and
    (2) binding partner II which is a labeled natural or artificial ligand.

11. An article as claimed in claim 10, in which the carrier protein in the recombinant fusion protein is the constant part of the heavy chain of human IgG1.

12. An article for a binding assay for investigating binding behavior of a cellular receptor protein to a labeled natural or artificial ligand comprising
    (1) a binding partner I which is a recombinant fusion protein comprising an extracellular domain of a cellular receptor linked to a carrier protein, wherein said carrier protein is an immunoglobulin and further wherein said carrier protein is bound to a solid phase by an antiserum or monoclonal antibody thereby retaining binding activity of the receptor to a binding partner II, and
    (2) binding partner II which is a labeled natural or artificial ligand.

13. An article as claimed in claim 12, where the cellular receptor is a cytokine receptor.

14. An article as claimed in claim 12, where the cellular receptor is a growth factor receptor.

15. An article as claimed in claim 12, where the cellular receptor is a hormone receptor.

16. An article as claimed in claim 12, where the cellular receptor is a neurotransmitter receptor.

17. An article as claimed in claim 12, where the cellular receptor is the receptor for a pathogenic organism.

18. An article as claimed in claim 12, in which the cellular receptor in the recombinant fusion protein is a cell adhesion molecule.

19. A method for detecting or measuring a ligand comprising
    (1) reacting binding partner I, which is a recombinant fusion protein comprising a cellular receptor linked to a carrier protein, wherein said carrier protein is an immunoglobulin and further wherein said carrier protein is bound to a solid phase by an antiserum or monoclonal antibody thereby retaining binding activity of the receptor to a binding partner II, with said binding partner II, which is a labeled natural or artificial ligand, and
    (2) detecting binding between binding partner I and binding partner II as an indication of the presence or amount of said ligand.

20. A method according to claim 19 for receptor screening for the identification of a natural or synthetic agonist or antagonist of an interaction, further comprising adding said natural or synthetic agonist or antagonist in step (1).

21. A method according to claim 19 for the characterization of an antibody directed against one of the two binding partners, further comprising adding said antibody in step (1).

22. A method according to claim 19 for testing for binding activity of a soluble cellular receptor, further comprising adding said soluble cellular receptor in step (1).

23. A method according to claim 19 for testing for binding activity of an unlabeled ligand, further comprising adding said unlabeled ligand in step (1).

24. A method according to claim 23, wherein said unlabelled ligand has a specific modification.

25. A method according to claim 23, wherein the method further quantitatively determines said labelled ligand.

26. A method according to claim 19 for the identification of a substance which influences the interaction of a ligand with its cellular receptor, further comprising adding said substance in step (1).

* * * * *